(12) United States Patent
Horbury et al.

(10) Patent No.: US 7,842,807 B2
(45) Date of Patent: *Nov. 30, 2010

(54) PROCESS FOR PREPARING THE CALCIUM SALT OF ROSUVASTATIN

(75) Inventors: John Horbury, Bristol (GB); Nigel Philip Taylor, Macclesfield (GB)

(73) Assignee: AstraZeneca UK Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/371,359

(22) Filed: Feb. 13, 2009

(65) Prior Publication Data

US 2009/0286819 A1 Nov. 19, 2009

Related U.S. Application Data

(63) Continuation of application No. 10/524,235, filed as application No. PCT/GB03/03463 on Aug. 7, 2003, now Pat. No. 7,511,140.

(30) Foreign Application Priority Data

Aug. 13, 2002 (GB) ................. 0218781.3

(51) Int. Cl.
 *C07D 239/42* (2006.01)
 *A61K 31/505* (2006.01)
 *A61P 3/06* (2006.01)

(52) U.S. Cl. .............. 544/297; 544/330; 544/332; 514/275

(58) Field of Classification Search ............. 544/297, 544/330, 332; 514/275
See application file for complete search history.

(56) References Cited

U.S. PATENT DOCUMENTS

| 4,645,858 | A | * | 2/1987 | Lowrie et al. |
| 4,970,313 | A | * | 11/1990 | Wess et al. |
| 4,977,279 | A | * | 12/1990 | Wess et al. |
| 5,026,698 | A | * | 6/1991 | Fujikawa et al. |
| 5,260,440 | A | * | 11/1993 | Hirai et al. |
| 5,278,313 | A | * | 1/1994 | Thottathil et al. |
| 5,399,722 | A | * | 3/1995 | Beck et al. |
| 5,594,153 | A | * | 1/1997 | Thottathil et al. |
| 6,278,001 | B1 | * | 8/2001 | Solladie et al. |
| 6,331,641 | B1 | * | 12/2001 | Taoka et al. |
| 6,784,171 | B2 | * | 8/2004 | Taylor et al. |
| 6,844,437 | B1 | * | 1/2005 | Taylor et al. |
| 6,870,059 | B2 | * | 3/2005 | Kooistra et al. |
| 6,875,867 | B2 | * | 4/2005 | Brodfuehrer et al. |
| 7,157,255 | B2 | * | 1/2007 | Blacker et al. |
| 7,304,156 | B2 | * | 12/2007 | Matsushita et al. |
| 7,416,865 | B2 | * | 8/2008 | Blacker et al. |
| 7,442,811 | B2 | * | 10/2008 | Bakel Van et al. |
| 7,511,140 | B2 | * | 3/2009 | Horbury et al. ............ 544/297 |
| 7,524,955 | B2 | * | 4/2009 | Newton et al. |
| 7,642,363 | B2 | * | 1/2010 | Kooistra et al. |
| 2003/0018199 | A1 | * | 1/2003 | Brodfuehrer et al. |
| 2003/0114685 | A1 | * | 6/2003 | Niddam-Hildesheim et al. |
| 2005/0090674 | A1 | * | 4/2005 | Hof |
| 2005/0124639 | A1 | * | 6/2005 | Joshi et al. |
| 2005/0209259 | A1 | * | 9/2005 | Huang |
| 2006/0004200 | A1 | * | 1/2006 | Gudipati et al. |
| 2006/0293355 | A1 | * | 12/2006 | Booth et al. |
| 2007/0105882 | A1 | * | 5/2007 | Black et al. |
| 2007/0255060 | A1 | * | 11/2007 | Okada et al. |
| 2008/0058520 | A1 | * | 3/2008 | Matsushita et al. |
| 2008/0188657 | A1 | * | 8/2008 | Lenger |
| 2008/0207903 | A1 | * | 8/2008 | Butters et al. |
| 2008/0221323 | A1 | * | 9/2008 | Crabb et al. |
| 2008/0280336 | A1 | * | 11/2008 | Blacker et al. |
| 2009/0264654 | A1 | * | 10/2009 | Newton et al. |
| 2009/0286819 | A1 | * | 11/2009 | Horbury et al. |

FOREIGN PATENT DOCUMENTS

| CA | 2545316 | * | 5/2005 |
| EP | 0521471 | * | 10/2000 |
| WO | WO 90/03973 | * | 4/1990 |
| WO | WO 93/08823 | * | 5/1993 |
| WO | WO 97/03959 | * | 2/1997 |
| WO | WO 97/19917 | * | 6/1997 |
| WO | WO 97/49681 | * | 12/1997 |
| WO | WO 00/42024 | * | 7/2000 |
| WO | WO 00/49014 | * | 8/2000 |
| WO | WO 01/22962 | * | 4/2001 |
| WO | WO 01/36384 | * | 5/2001 |
| WO | WO 01/54669 | * | 8/2001 |
| WO | WO 01/60804 | | 8/2001 |

(Continued)

OTHER PUBLICATIONS

Hiyama et al. "Synthesis of Artificial HMG-CoA Reductase Inhibitors Based on the Olefination Strategy" Bull. Chem. Soc. Jpn. 68 (1):364-372 (1995).

(Continued)

*Primary Examiner*—Venkataraman Balasubramanian
(74) *Attorney, Agent, or Firm*—Morgan Lewis & Bockius LLP

(57) ABSTRACT

An improved process for manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which is useful for the production of a pharmaceutical useful in the treatment of, inter alia, hypercholesterolemia, hyperlipoproteinemia and atherosclerosis, is described.

11 Claims, No Drawings

FOREIGN PATENT DOCUMENTS

| | | |
|---|---|---|
| WO | WO 01/72706 | 10/2001 |
| WO | WO 01/85702 | 11/2001 |
| WO | WO 01/85975 | 11/2001 |
| WO | WO 02/06266 | 1/2002 |
| WO | WO 02/30415 | 4/2002 |
| WO | WO 02/43667 | 6/2002 |
| WO | WO 02/43732 | 6/2002 |
| WO | WO 02/072566 | 9/2002 |
| WO | WO 02/083637 | 10/2002 |
| WO | WO 02/098854 | 12/2002 |
| WO | WO 03/006439 | 1/2003 |
| WO | WO 03/016317 | 2/2003 |
| WO | WO 03/018555 | 3/2003 |
| WO | WO 03/026573 | 4/2003 |
| WO | WO 03/059901 | 7/2003 |
| WO | WO 03/087112 | 10/2003 |
| WO | WO 03/097614 | 11/2003 |
| WO | WO 03/106447 | 12/2003 |
| WO | WO 2004/014872 | 2/2004 |
| WO | WO 2004/052867 | 6/2004 |
| WO | WO 2004/054986 | 7/2004 |
| WO | WO 2004/089895 | 10/2004 |
| WO | WO 2004/103977 | 12/2004 |
| WO | WO 2004/108691 | 12/2004 |
| WO | WO 2005/005384 | 1/2005 |
| WO | WO 2005/023778 | 3/2005 |
| WO | WO 2005/023779 | 3/2005 |
| WO | WO 2005/028450 | 3/2005 |
| WO | WO 2005/030215 | 4/2005 |
| WO | WO 2005/040134 | 5/2005 |
| WO | WO 2005/042522 | 5/2005 |
| WO | WO 2005/047276 | 5/2005 |
| WO | WO 2005/051921 | 6/2005 |
| WO | WO 2005/054207 | 6/2005 |
| WO | WO 2005/056534 | 6/2005 |
| WO | WO 2005/063728 | 7/2005 |
| WO | WO 2005/068435 | 7/2005 |
| WO | WO 2005/077916 | 8/2005 |
| WO | WO 2005/077917 | 8/2005 |
| WO | WO 2005/092867 | 10/2005 |
| WO | WO 2006/017357 | 2/2006 |
| WO | WO 2006/035277 | 4/2006 |
| WO | WO 2006/067456 | 6/2006 |
| WO | WO 2006/079611 | 8/2006 |
| WO | WO 2006/089401 | 8/2006 |
| WO | WO 2007/007119 * | 1/2007 |

OTHER PUBLICATIONS

Kaneko et al. "Preparation of optically active 5,6-epoxyhexanoic acid esters as materials for physiologically active substances" Chemical Abstracts + Indexes, American Chemical Society, Columbus, US 118(11):832 (1993).

Menges et al. "Oxidative Degradation of γ-Butyrolactons into 1,3-Diols via a Criegee Rearrangement of Peroxosulfonates. An Enantioselective Synthesis of Compactin Lactone and its Diastereomer" Synlett 12:901-905 (1993).

Minami et al. "A Novel Enantioselective Synthesis of HMG Co-A Reductase Inhibitor NK-104 and a Related Compound" Tetrahedron letters 33(49):7525-7526 (1992).

Minami et al. "Stereoselective Reduction of β,-Diketo Esters Derived From Tartaric Acid. A Facile Route to Optically Active 6-oxo-3,5-syn-isopropylidenedioxyhexanoate, a Versatile Synthetic Intermediate of Artificial HMG Co-A Reductase Inhibitors" Tetrahedron Letters 34(3):513-516 (1993).

Moore et al. "Biosynthesis of the hypocholesterolemic agent mevinolin by Aspergillus terreus. Determination of the origin of carbon, hydrogen, and oxygen atoms by carbon-13 NMR and mass spectrometry" J. Am. Chem. Soc. 107(12): 3694-3701 (1985).

Nezasa et al. "Pharmacokinetics and disposition of rosuvastatin, a new 3-hydroxy-3-methylglutaryl coenzyme A reductase inhibitor, in rat" Xenobiotica 32(8):715-727 (2002).

Prasad et al. "A novel diastereroselective synthesis of lactone moiety of compactin" Tetrahedron Letters 25(23):2435-2438 (1984).

Presentation given at the 20th International Congress of Heterocyclic Chemistry in Palermo, Aug. 1-5, 2005.

Presentation given at the Gordon Conference on Heterocyclic Compounds, Salve Regina University, Newport, Rhode Island, Jul. 4-9, 2004.

Sakaki et al. "Lipase-catalyzed asymmetric synthesis of 6-(3-chloro-2-hydroxypropyl)-1,3-dioxin-4-ones and their conversion to chiral 5,6-epoxyhexanoates" Tetrahedron: Asymmetry 2(5):343-346 (1991).

Shao et al. "Asymmetric hydrogenation of 3,5-Dioxoesters catalyzed by Ru-binap complex: A short step asymmetric synthesis of 6-substituted 5,6-dihydro-2-pyrones" Tetrahedron 49(10):1997-2010 (1993).

Solladié et al. "Chrial Sulfoxides in Asymmetric Synthesis: Enantioselective Synthesis of the Lactonic Moiety of (+)-Compactin and (+)-Mevinolin. Application of a Compactin Analogue" J. Org. Chem. 60:7774-7777 (1995).

Watanabe et al. "Synthesis and Biological Activity of Methanesulfonamide Pyrimidine- and N-Methanesulfonyl Pyrrole-Substituted 3,5-Dihydroxy-6-heptenoates, a Novel Series of HMG-CoA Reductase Inhibitors" Bioorganic & Medicinal Chemistry 5(2):437-444 (1997).

Wess et al. "Stereoselective Synthesis of HR 780 A New Highly Potent HMG-CoA Reductase Inhibitor", Tetrahedron Letters 31(18): 2545-2548 (1990).

* cited by examiner

PROCESS FOR PREPARING THE CALCIUM SALT OF ROSUVASTATIN

RELATED APPLICATIONS

This is a Continuation Application of U.S. application Ser. No. 10/524,235, filed Aug. 18, 2005, now U.S. Pat. No. 7,511,140, which is a U.S. National Phase Application of International PCT Application No. PCT/GB2003/003463 filed Aug. 7, 2003 which claims the benefit of British Application No. 0218781.3, filed Aug. 13, 2002, all of which are herein incorporated by reference in their entireties.

This invention concerns improvements to a chemical process, particularly a chemical process for manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt (illustrated below), which is useful for the production of a pharmaceutical useful in the treatment of, inter alia, hypercholesterolemia, hyperlipoproteinemia and atherosclerosis.

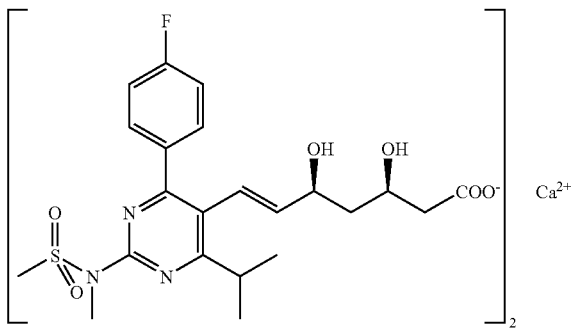

Compound (E)-7-[4-(4-fluorophenyl)-6-isopropyl-2-[methyl(methylsulfonyl)amino]pyrimidin-5-yl](3R,5S)-3,5-dihydroxyhept-6-enoic acid (hereinafter referred to as the 'Agent') and its sodium salt and calcium salt were disclosed in European Patent 0521471. This patent also describes a process for the synthesis of the calcium salt of the Agent, the final stage of which is the conversion of the sodium salt of the Agent into the calcium salt. The calcium salt thus formed is then collected and dried and may be processed further as required.

This conversion of the sodium salt into the calcium salt, followed by collection and drying is also described in our International Patent Application WO 00/49014.

The process as described in both of the above documents comprises dropwise addition of an aqueous solution of calcium chloride to an aqueous solution of the sodium salt at 20° C., stirring of the resulting mixture for, for example 45 minutes, and then isolation of the product precipitate by filtration. The filtered product is washed and dried under reduced pressure at 40° C. Efficient washing of the product is essential to ensure removal of sodium chloride produced as a by-product of the reaction. Filtration and drying are then required to give a final product suitable for use as a pharmaceutical.

Precipitation at 20° C. according to the process described in these applications produces a product which has a physical form such that it is difficult and slow (ie inefficient) to filter, and retains a substantial quantity of water after filtration. This necessitates extensive drying in order to obtain a final product suitable for use as a pharmaceutical. Although manageable on a small (laboratory) or medium scale, on a manufacturing scale, handling a product requiring such treatment is highly problematic and is undesirable in terms of manufacturing output and, potentially, product quality.

We have discovered a surprising improvement to the process of manufacturing the calcium salt, which results in improved efficiency of filtration of the product during the isolation process.

In general, reference to improved efficiency of filtration refers to achieving removal of more solvent, such as water, from the product during filtration and optionally to filtration being faster. It will be appreciated that in general a product which is isolated with a low solvent (such as water) content requires less drying time after isolation than one with a higher solvent content in order to achieve the same overall endpoint. It will also be appreciated that the advantages associated with efficient filtration during the initial isolation of the product will also be realised for filtrations carried out as part of any subsequent washing process.

It will be appreciated therefore that the process of the current invention results in significant manufacturing advantages, for example increased manufacturing output.

Accordingly, the present invention provides an improved process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid, wherein the process parameters are selected to give a product which demonstrates improved efficiency of filtration.

Suitable water soluble salts may be metal salts, for example an alkali metal salt, such as sodium, lithium or potassium; or an ammonium salt or an organic amine salt such as methylamine or TRIS (tris(hydroxymethyl)aminomethane) salt. Preferred salts are the sodium salt, potassium and ammonium salts. Further preferred salts are the ammonium, methylamine and TRIS salts. A further preferred salt is the TRIS salt. Most preferred is the sodium salt.

For the avoidance of doubt, the solution of the water soluble salt may be produced by dissolution of a solid form of the salt in water. Alternatively the solution of the water soluble salt may be generated from (E)-7-[4-(4-fluorophenyl)-6-isopropyl-2-[methyl(methylsulfonyl)amino]pyrimidin-5-yl](3R,5S)-3,5-dihydroxyhept-6-enoic acid or a suitable derivative thereof, for example an alternative salt form. For example, where the water soluble salt is the sodium salt, it may be generated by treatment of an alternative salt (in solid form or as a suspension or a solution in water) such as an amine salt (for example ammonium or methylamine salt) with a sodium base, for example sodium carbonate or sodium hydroxide, preferably sodium hydroxide. Conveniently the sodium base is a solution in water. Similarly, other bases such as other alkali metal bases could be used to generate solutions of other water soluble salts.

In general, the solution of calcium chloride will be an aqueous or substantially aqueous solution. In general the solution of the water soluble salt will be an aqueous or substantially aqueous solution. By substantially aqueous solution herein, we mean a solution in water which may also contain small amounts of organic or inorganic compounds, for example arising from incomplete removal of solvent after the previous manufacturing stage. It will be understood that the presence of small amounts of organic or inorganic impurities may require adjustments to the process conditions as herein described (for example temperature) in order to obtain a product which can be filtered efficiently, but that any such adjustments would not require undue experimentation by the skilled man.

In general, process parameters which are features of the present invention comprise the temperature at which the two solutions are added together and optionally the period of time for which the two solutions are mixed.

In general, the mixing of the two solutions is achieved by addition of the calcium chloride solution to the solution of the water soluble salt of the Agent. In general, the addition of the calcium chloride solution is carried out over a period of time, hereinafter referred to as the 'addition time'. After addition of the calcium chloride solution has been completed, the mixture is generally stirred for a period of time hereinafter referred to as the 'hold time'. Reference hereinbefore to mixing of the calcium chloride solution with the water-soluble salt solution for a period of time is to be understood to refer to mixing these solutions for the combination of the addition time and the hold time.

In one aspect of the invention, the addition temperature is selected to give a product which demonstrates improved efficiency of filtration.

In one embodiment, the addition is carried out at a temperature (hereinafter referred to as 'the addition temperature') of between 30 and approximately 45° C., preferably between 32 and 43° C., more preferably between 35 and 42° C., and most preferably at approximately 40° C. In another embodiment, the addition temperature is between 30 and 43° C., conveniently between 30 and 40° C.

Therefore in one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature is selected to give a product which demonstrates improved efficiency of filtration.

The calcium chloride solution may be heated before it is added to the water soluble salt solution, however it will be understood that such heating should not result in the addition temperature being elevated above 45° C., and preferably not above 40° C. It will be understood that the addition temperature refers to the temperature of the water soluble salt solution.

In one aspect of the invention, the addition temperature, addition time and hold time are selected to give a product which demonstrates improved efficiency of filtration.

In one embodiment of the invention the addition time is 5 to 60 minutes, in particular 15-30 minutes.

In one embodiment, the hold time is at least 10 minutes. In another embodiment, the hold time is at least 15 minutes. In a further embodiment, the hold time is at least 30 minutes. It is convenient to stir the mixture during the hold time at approximately the addition temperature.

Therefore in one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature, addition time and hold time (all as hereinbefore defined) are selected to give a product which demonstrates improved efficiency of filtration.

In particular, the calcium chloride is added at a temperature of between 32 and 43° C. over a period of 15 to 30 minutes, the mixture held at a temperature of between 32 and 43° C. over a period of at least 15 minutes, then the product is isolated by filtration and then dried.

In particular, the calcium chloride is added at a temperature of between 32 and 43° C. over a period of 15 to 30 minutes, the mixture held at a temperature of between 32 and 43° C. over a period of at least 30 minutes, then the product is isolated by filtration and then dried.

In a further aspect of the invention, the addition temperature and hold time are selected to give a product which demonstrates improved efficiency of filtration.

In particular, the addition temperature is 32 to 43° C. and the hold time is at least 30 minutes. In another aspect, the addition temperature is 32 to 43° C. and the hold time is at least 15 minutes.

In a further aspect of the invention, the addition temperature is selected to give a product which demonstrates improved efficiency of filtration. In particular, the addition temperature is 32 to 43° C. In a further aspect the temperature is approximately 40° C.

In a further aspect of the invention, the addition time is selected to give a product which demonstrates improved efficiency of filtration. In particular, the addition time is 15 to 30 minutes.

In a further aspect of the invention, the hold time is selected to give a product which demonstrates improved efficiency of filtration. In particular, the hold time is at least 15 minutes.

As previously mentioned, the process of the invention results in a more efficient filtration process such that the solid product isolated on the filter has a reduced water content (and therefore higher 'paste strength') than the equivalent product obtained after precipitation at 20° C. Typically, the paste strengths obtained with the process of the present invention will be greater than 45% w/w. As a consequence of increased paste strength, the final drying step after removal from the filter may be of shorter duration and hence manufacturing output may increase.

Therefore in one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature, addition time and hold time are selected to give a product with a paste strength of more than about 45% w/w, such as about 50% w/w, or about 55% w/w, or about 60% w/w, or about 65% w/w, or about 70% w/w, or about 75% w/w, or about 80% w/w, or about 85% w/w, or about 90% w/w, or about 95% w/w.

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 5 to 60 minutes at a temperature of 30 to 45° C., holding the mixture at a temperature of 30 to 45° C. for at least 10 minutes, filtering, optionally washing, and drying of the resultant product.

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 15 to 30 minutes at a temperature of 32 to 43° C., holding the mixture at a temperature of 32 to 43° C. for at least 15 minutes, filtering, optionally washing, and drying of the resultant product.

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 30 to 45° C., filtering, optionally washing, and drying of the resultant product.

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 32 to 43° C., filtering, optionally washing, and drying of the resultant product.

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 5 to 60 minutes at a temperature of 30 to 45° C., holding the mixture at a temperature of 30 to 45° C. for at least 10 minutes, filtering, optionally washing, and drying of the resultant product to give a product with a paste strength of more than about 45% w/w, such as about 50% w/w, or about 55% w/w, or about 60% w/w, or about 65% w/w, or about 70% w/w, or about 75% w/w, or about 80% w/w, or about 85% w/w, or about 90% w/w, or about 95% w/w.

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 15 to 30 minutes at a temperature of 32 to 43° C., holding the mixture at a temperature of 32 to 43° C. for at least 15 minutes, filtering, optionally washing, and drying of the resultant product to give a product with a paste strength of more than about 45% w/w, such as about 50% w/w, or about 55% w/w, or about 60% w/w, or about 65% w/w, or about 70% w/w, or about 75% w/w, or about 80% w/w, or about 85% w/w, or about 90% w/w, or about 95% w/w.

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 30 to 45° C., filtering, optionally washing, and drying of the resultant product to give a product with a paste strength of more than about 45% w/w, such as about 50% w/w, or about 55% w/w, or about 60% w/w, or about 65% w/w, or about 70% w/w, or about 75% w/w, or about 80% w/w, or about 85% w/w, or about 90% w/w, or about 95% w/w.

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 32 to 43° C., filtering, optionally washing, and drying of the resultant product to give a product with a paste strength of more than about 45% w/w, such as about 50% w/w, or about 55% w/w, or about 60% w/w, or about 65% w/w, or about 70% w/w, or about 75% w/w, or about 80% w/w, or about 85% w/w, or about 90% w/w, or about 95% w/w.

A further aspect of the invention provides a product obtainable by the process of the present invention.

Another aspect of the invention provides a product obtained by the process of the present invention.

Another aspect of the invention provides a product of the process of the present invention, isolated on a filter with a paste strength of greater than 45% w/w. Another aspect of the invention provides a product of the process of the present invention, isolated on a filter with a paste strength of greater than 50% w/w. Another aspect of the invention provides a product of the process of the present invention, isolated on a filter with a paste strength of greater than 70% w/w. Another aspect of the invention provides a product of the process of the present invention, isolated on a filter with a paste strength of greater than 80% w/w. It will be understood that the term 'paste strength' is defined as the % w/w of the product compound in the isolated solid product (with the balance comprising substantially of water).

Suitable conditions for isolating the product include pressure filter or centrifuge. The product can be dried in a pressure filter or centrifuge under nitrogen flow or by vacuum or discharged from the isolation equipment into a cone drier, for example, and dried under vacuum.

The observed improved efficiency of filtration, as described hereinbefore, which is achieved with the process of the invention, results in whole or in part from the solid product obtained possessing different physical form to that achieved by the process described in the prior art. This different physical form is provided as a further aspect of the invention. It is to be understood that the solid product obtained both from the inventive process and from the prior art process as described, is amorphous and thus any difference in physical form arising from the inventive process is not due to crystallinity.

The different physical form is manifested by an increased particle size of the product arising from the inventive process. The particle size may be illustrated for example by measurement of the specific surface area of the solid, by any method known in the art. The specific surface area of product obtained from the process of the invention is generally less than approximately 1 $m^2/g$ (as measured by Fisher technique, see for example Gooden, Ernest L and Smith Charles M, *Ind Eng Chem, Anal Ed.* 12, 479-482 (1940), and Corman P. C., *J. Soc. Chem. Ind*, 57, 225-239). In contrast, the specific surface area of product obtained from the process of the prior art (at lower temperatures, for example 20° C.) is generally greater than or equal to approximately 2 $m^2/g$. It will be appreciated that generation of material of lower specific surface area will generally result in a product of a higher paste strength after a given filtration time. Alternatively, with the material of low specific area, the filtration times needed to achieve a given paste strength are generally shorter. Generally with the process of the invention, a paste strength of at least 50% can be achieved in a maximum of 15 minutes filtration on a laboratory scale.

In one aspect the specific surface area (SSA) as measured by the Fisher technique is less than 1 $m^2/g$. In another aspect the SSA is less than 0.9 $m^2/g$. In another aspect the SSA is less than 0.8 $m^2/g$. In another aspect the SSA is less than 0.7 $m^2/g$. In another aspect the SSA is less than 0.6 $m^2/g$. In another aspect the SSA is less than 0.5 $m^2/g$. In another aspect the SSA is less than 0.4 $m^2/g$. In another aspect the SSA is less than 0.5 $m^2/g$. In another aspect the SSA is less than 0.3 $m^2/g$.

It will be appreciated that the increased particle size of the product obtained from the process of the invention may also result in advantageous properties in the material obtained after filtration, optional washing and drying. For example, as particle size increases, the filtered, dried material may flow more easily, and/or be easier to mill, and/or be easier to formulate (for example by compression into a tablet formulation by any method known in the art).

In one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature is selected to give a product with a specific surface area of less than 1 $m^2/g$ (measured by Fisher technique).

In one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature is selected to give a product with a specific surface area of less than 0.8 $m^2/g$ (measured by Fisher technique).

In one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature is selected to give a product with a specific surface area of less than 0.6 $m^2/g$ (measured by Fisher technique).

In one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature is selected to give a product with a specific surface area of less than 0.5 $m^2/g$ (measured by Fisher technique).

In one aspect, the present invention provides a process for the manufacture of (E)-7-[4-(4-fluorophenyl)-6-isopropyl-2-[methyl(methylsulfanyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature is selected to give a product with a specific surface area of less than 0.4 $m^2/g$ (measured by Fisher technique).

In one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature, addition time and hold time (all as hereinbefore defined) are selected to give a product with a specific surface area of less than 1 $m^2/g$ (measured by Fisher technique).

In one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature, addition time and hold time (all as hereinbefore defined) are selected to give a product with a specific surface area of less than 0.8 $m^2/g$ (measured by Fisher technique).

In one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature, addition time and hold time (all as hereinbefore defined) are selected to give a product with a specific surface area of less than 0.8 $m^2/g$ (measured by Fisher technique).

In one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature, addition time and hold time (all as hereinbefore defined) are selected to give a product with a specific surface area of less than 0.5 m$^2$/g (measured by Fisher technique).

In one aspect, the present invention provides a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid under conditions such that the addition temperature, addition time and hold time (all as hereinbefore defined) are selected to give a product with a specific surface area of less than 0.4 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 30 to 45° C., filtering, optionally washing, and drying of the resultant product to give a product with a specific surface area of less than 1 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 30 to 45° C., filtering, optionally washing, and drying of the resultant product to give a product with a specific surface area of less than 0.8 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 30 to 45° C., filtering, optionally washing, and drying of the resultant product to give a product with a specific surface area of less than 0.6 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 30 to 45° C., filtering, optionally washing, and drying of the resultant product to give a product with a specific surface area of less than 0.5 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 30 to 45° C., filtering, optionally washing, and drying of the resultant product to give a product with a specific surface area of less than 0.4 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 32 to 43° C., filtering, optionally washing, and drying of the resultant product to give a product with a specific surface area of less than 1 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 32 to 43° C., filtering, optionally washing, and drying of the resultant product to give a product with a specific surface area of less than 0.8 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 32 to 43° C., filtering, optionally washing, and drying of the resultant product to give a product with a specific surface area of less than 0.6 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 32 to 43° C., filtering, optionally washing, and drying of the resultant product to give a product with a specific surface area of less than 0.5 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of 32 to 43° C., filtering, optionally washing, and drying of the resultant product to give a product with a specific surface area of less than 0.4 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of approximately 40° C., filtering, optionally washing, and drying of the resultant product to give a product with a specific surface area of less than 1 m²/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of approximately 40° C., filtering, optionally washing, and drying of the resultant product to give a product with a specific surface area of less than 0.8 m²/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of approximately 40° C., filtering, optionally washing, and drying of the resultant product to give a product with a specific surface area of less than 0.6 m²/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature of approximately 40° C., filtering, optionally washing, and drying of the resultant product to give a product with a specific surface area of less than 0.5 m²/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid at a temperature approximately 40° C., filtering, optionally washing, and drying of the resultant product to give a product with a specific surface area of less than 0.4 m²/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 5 to 60 minutes at a temperature of 30 to 45° C., holding the mixture at a temperature of 30 to 45° C. for at least 10 minutes, filtering, optionally washing, and drying of the resultant product to give a product with a specific surface area of less than 1 m²/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 5 to 60 minutes at a temperature of 30 to 45° C., holding the mixture at a temperature of 30 to 45° C. for at least 10 minutes, filtering, optionally washing, and drying of the resultant product to give a product with a specific surface area of less than 0.8 m²/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 5 to 60 minutes at a temperature of 30 to 45° C., holding the mixture at a temperature of 30 to 45° C. for at least 10 minutes, filtering, optionally washing, and drying of the resultant product to give a product with a specific surface area of less than 0.6 m²/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 5 to 60 minutes at a temperature of 30 to 45° C., holding the mixture at a temperature of 30 to 45° C. for at least 10 minutes, filtering, optionally washing, and drying of the resultant product to give a product with a specific surface area of less than 0.5 m²/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 5 to 60 minutes at a temperature of 30 to 45° C., holding the mixture at a temperature of 30 to 45° C. for at least 10 minutes, filtering, optionally washing, and drying of the resultant product to give a product with a specific surface area of less than 0.4 m²/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 15 to 30 minutes at a temperature of 32 to 43° C., holding the mixture at a temperature of 32 to 43° C. for at least 15 minutes, filtering, optionally washing, and drying of the resultant product to give a product with a specific surface area of less than 1 m²/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 15 to 30 minutes at a temperature of 32 to 43° C., holding the mixture at a temperature of 32 to 43° C. for at least 15 minutes, filtering, optionally washing, and drying of the resultant product to give a product with a specific surface area of less than 0.8 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 15 to 30 minutes at a temperature of 32 to 43° C., holding the mixture at a temperature of 32 to 43° C. for at least 15 minutes, filtering, optionally washing, and drying of the resultant product to give a product with a specific surface area of less than 0.6 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 15 to 30 minutes at a temperature of 32 to 43° C., holding the mixture at a temperature of 32 to 43° C. for at least 15 minutes, filtering, optionally washing, and drying of the resultant product to give a product with a specific surface area of less than 0.5 m$^2$/g (measured by Fisher technique).

In a further aspect of the invention is provided a process for the manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which process comprises addition of a solution of calcium chloride to a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid over 15 to 30 minutes at a temperature of 32 to 43° C., holding the mixture at a temperature of 32 to 43° C. for at least 15 minutes, filtering, optionally washing, and drying of the resultant product to give a product with a specific surface area of less than 0.4 m$^2$/g (measured by Fisher technique).

A preferred aspect of the present invention provides a process comprising mixing of a solution of calcium chloride with a solution of a water-soluble salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid such that the addition temperature, addition time and hold time are adjusted to give a product with a specific surface area such that isolation of the product is optimised. By isolation of the product we mean filtering, optionally washing and drying of the product.

The product obtainable by the process of the invention may be administered to a warm-blooded animal, particularly a human, in need thereof for treatment of a disease in which HMG CoA reductase is implicated, in the form of a conventional pharmaceutical composition. Therefore in another aspect of the invention, there is provided a pharmaceutical composition comprising a product obtainable by the process of the invention as described above in admixture with a pharmaceutically acceptable diluent or carrier. In another aspect of the invention, there is provided a pharmaceutical composition comprising a product obtained by the process of the invention as described above in admixture with a pharmaceutically acceptable diluent or carrier. Suitable pharmaceutically acceptable diluents or carriers are described in our patent applications WO 01/60804 and WO 01/54668.

The invention is further illustrated, but not limited by the following examples.

EXAMPLE 1

Preparation Starting from Methylamine Salt

The experiments which generated the data presented below were carried out as follows. (E)-7-[4-(4-fluorophenyl)-6-isopropyl-2-[methyl(methylsulfonyl)amino]pyrimidin-5-yl](3R,5S)-3,5-dihydroxyhept-6-enoic acid methylamine salt, 2M sodium hydroxide solution (0.93 mol equivalents) and water were mixed together, the solution evaporated to low volume under vacuum at <40° C. to remove methylamine and then made up with water to give a concentration of the sodium salt of 0.2M. Aliquots of the stock solutions were taken and the calcium salt precipitated by dropwise addition of a solution of calcium chloride (0.6 mol eq of a 0.7M aqueous solution) using the conditions (temperature, addition time, hold time and agitation rate) according to the experimental design described below. The reaction mixture was then cooled to 20° C., filtered, washed with three portions of water and deliquored for a standard time before measuring the paste strength of the isolated material.

Data

The data presented below illustrate the improvement in paste strength associated with temperature, addition time and hold time. The data were generated during experiments carried out as part of a factorial experimental design using essentially the process described above.

| Experiment ID # | NaOH (eq) | Agitation (rpm) | Temp (° C.) | Addition time (mins) | Hold time (mins) | Paste Strength (% w/w) |
|---|---|---|---|---|---|---|
| 1 | 0.99 | 550 | 32 | 15 | 10 | 41.4% |
| 2 | 0.93 | 550 | 40 | 15 | 10 | 55.9% |
| 3 | 0.96 | 400 | 36 | 6 | 10 | 42.7% |
| 4 | 0.99 | 550 | 40 | 0 | 10 | 48.7% |
| 5 | 0.99 | 550 | 40 | 15 | 30 | 62.9% |
| 6 | 0.96 | 400 | 36 | 6 | 10 | 42.4% |
| 7 | 0.93 | 250 | 32 | 0 | 30 | 40.5% |
| 8 | 0.99 | 250 | 32 | 15 | 30 | 39.5% |
| 9 | 0.96 | 400 | 36 | 6 | 10 | 43.3% |
| 10 | 0.99 | 250 | 40 | 15 | 10 | 53.9% |
| 11 | 0.93 | 550 | 32 | 0 | 10 | 34.8% |
| 12 | 0.93 | 250 | 40 | 0 | 10 | 53.9% |
| 13 | 0.93 | 550 | 32 | 15 | 30 | 51.6% |
| 14 | 0.99 | 250 | 40 | 0 | 30 | 60.7% |
| 15 | 0.93 | 250 | 32 | 15 | 10 | 42.9% |
| 16 | 0.93 | 250 | 40 | 15 | 30 | 62.0% |
| 17 | 0.99 | 550 | 32 | 0 | 30 | 37.0% |
| 18 | 0.99 | 250 | 32 | 0 | 10 | 29.1% |
| 19 | 0.96 | 400 | 36 | 6 | 10 | 42.9% |
| 20 | 0.93 | 550 | 40 | 0 | 30 | 64.6% |

EXAMPLE 2

Preparation Starting from the Methylamine Salt at 40° C.

Sodium hydroxide (8% w/w aqueous solution; 13.6 ml) was added to a stirred mixture of (E)-7-[4-(4-fluorophenyl)-

6-isopropyl-2-[methyl(methylsulfonyl)amino]pyrimidin-5-yl](3R,5S)-3,5-dihydroxyhept-6-enoic acid methylammonium salt (15.0 g) in water (117 ml, purified). Water (2 ml, purified) was added as a line wash prior to removal of the methylamine by vacuum distillation (maximum batch temperature 40° C.). Water (45 ml, purified) was added, and a further vacuum distillation carried out (maximum batch temperature 40° C.). Water (55 ml, purified) was again added to the mixture prior to filtration through a glass fibre pad. Purified water was added to return the total volume to the initial volume prior to the distillations. A solution of calcium chloride dihydrate (2.58 g) in water (25 ml, purified) was added dropwise over 20 minutes at 40° C. The mixture was held at 40° C. for 15 minutes, cooled to 20° C. over one hour and then stirred 20° C. prior to isolation by filtration. The solid was washed three times with water (45 ml, purified) and dried under nitrogen in vacuo at ambient temperature to give non-crystalline calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid.

Preparation Starting from the Methylamine Salt at 20° C.

Sodium hydroxide (8% w/w aqueous solution; 13.6 ml) was added to a stirred mixture of (E)-7-[4-(4-fluorophenyl)-6-isopropyl-2-[methyl(methylsulfonyl)amino]pyrimidin-5-yl](3R,5S)-3,5-dihydroxyhept-6-enoic acid methylammonium salt (15.0 g) in water (117 ml, purified). Water (2 ml, purified) was added as a line wash prior to removal of the methylamine by vacuum distillation (maximum batch temperature 40° C.). Water (45 ml, purified) was added, and a further vacuum distillation carried out (maximum batch temperature 40° C.). Water (55 ml, purified) was again added to the mixture prior to filtration through a glass fibre pad. Purified water was added to return the total volume to the initial volume prior to the distillations. A solution of calcium chloride dihydrate (2.58 g) in water (25 ml, purified) was added dropwise over 20 minutes at 20° C. The mixture was stirred for two hours prior to isolation by filtration. The solid was washed three times with water (45 ml, purified) and dried under nitrogen in vacuo at ambient temperature to give non-crystalline calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid.

The methylamine salt used as the starting material for Examples 1 and 2 may be prepared as described in WO 00/49104.

Comparative Paste Strengths

The paste strength of the sample prepared at 40° C. after 15 minutes of filtration was 80%. The paste strength of the sample prepared at 20° C. after 15 minutes of filtration was 14%.

EXAMPLE 3

Preparation Starting from the Ammonium Salt at 40° C.

Sodium hydroxide (8% w/w aqueous solution; 10.9 ml) was added to a stirred mixture of (E)-7-[4-(4-fluorophenyl)-6-isopropyl-2-[methyl(methylsulfonyl)amino]pyrimidin-5-yl](3R,5S)-3,5-dihydroxyhept-6-enoic acid ammonium salt (11.7 g) in degassed water (94 ml) at 20° C. and the mixture was stirred until a solution was obtained. The reaction mixture was concentrated under vacuum at <40° C. to remove ammonia, sufficient water added to return the total volume to the initial volume, and the reaction mixture heated to 40° C. A solution of calcium chloride dihydrate (2.1 g) in water (20 ml) was added dropwise at about 40° C. over 20 minutes. The mixture was stirred for 15 minutes, allowed to cool to 20° C. over 60 minutes, held at this temperature for a further 60 minutes and the resultant solid filtered. The solid was washed with water (100 ml) and dried under a flow of nitrogen to give non-crystalline calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid.

Preparation Starting from Ammonium Salt at 20° C.

Sodium hydroxide (8% w/w aqueous solution; 10.9 ml) was added to a stirred mixture of (E)-7-[4-(4-fluorophenyl)-6-isopropyl-2-[methyl(methylsulfonyl)amino]pyrimidin-5-yl](3R,5S)-3,5-dihydroxyhept-6-enoic acid ammonium salt (11.7 g) in degassed water (94 ml) at 20° C. and the mixture was stirred for until a solution was obtained. The reaction mixture was concentrated under vacuum at <40° C. to remove ammonia, sufficient water added to return the total volume to the initial volume, and the reaction mixture adjusted to 20° C. A solution of calcium chloride dihydrate (2.1 g) in water (20 ml) was added dropwise at about 20° C. over 20 minutes. The mixture was stirred for 1.5 h, and the resultant solid filtered. The solid was washed with water (100 ml) and dried under a flow of nitrogen to give non-crystalline calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid.

Preparation of (E)-7-[4-(4-fluorophenyl)-6-isopropyl-2-[methyl(methylsulfonyl)amino]pyrimidin-5-yl](3R,5S)-3,5-dihydroxyhept-6-enoic acid ammonium salt Hydrochloric acid (35 ml, 0.02M) was added to a solution of tert-butyl (6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate (prepared as described in WO 00/49014) (20.0 g, 34.6 mMol) in acetonitrile (140 ml) at 35° C. over 100 min and maintained at this temperature until reaction was complete. The reaction mixture was cooled to 25° C. then a solution of sodium hydroxide (1M, 38 ml) was added and the reaction mixture stirred for 1 hour. Water was added (100 ml) and acetonitrile removed under vacuum at about 40° C.; this procedure was repeated if necessary until all the acetonitrile had been removed. The mixture was filtered, n-butyl acetate (250 ml) was added and the mixture cooled to 0° C. The pH was adjusted to about pH 3.2 with hydrochloric acid (1M, approximately 38 g), the mixture stirred for about 15 minutes and the bottom aqueous phase removed. Further n-butylacetate (250 ml) was added to the organic phase and the solution again cooled to 0° C. before addition of a solution of ammonia in methanol (7N, 7.5 ml). The resulting mixture was warmed to 30° C. and maintained at this temperature for 30 minutes after the start of crystallisation, then cooled to 0° C. and maintained at this temperature for a further 2 hours. The solid was filtered, washed with n-butyl acetate and dried under vacuum to give the title compound (14.8 g, 86%).

Comparative Paste Strengths

The paste strength of the filtered product was measured after 5 minutes filtration. The sample prepared from ammonium salt at 40° C. had a paste strength of 75%. The sample prepared from ammonium salt at 20° C. had a paste strength of 45%.

EXAMPLE 4

Preparation Starting from TRIS Salt at 40° C.

(E)-7-[4-(4-Fluorophenyl)-6-isopropyl-2-[methyl(methylsulfonyl)amino]pyrimidin-5-yl](3R,5S)-3,5-dihydroxyhept-6-enoic acid TRIS salt (17.7 g) was dissolved in degassed water (120 ml) at 20° C. then the solution was heated to 40° C. A solution of calcium chloride dihydrate (2.6 g) in water (25 ml) was added dropwise at about 40° C. over 20 minutes. The mixture was stirred for 15 minutes, allowed to cool to 20° C. over 60 minutes, held at this temperature for a further 60 minutes and the resultant solid filtered. The solid was washed with water (140 ml) and dried under a flow of nitrogen to give non-crystalline calcium salt of (E)-7-[4-(4-fluorophenyl)-6-isopropyl-2-[methyl(methylsulfonyl) amino]pyrimidin-5-yl](3R,5S)-3,5-dihydroxyhept-6-enoic acid.

Preparation Starting from TRIS Salt at 20° C.

(E)-7-[4-(4-Fluorophenyl)-6-isopropyl-2-[methyl(methylsulfonyl)amino]pyrimidin-5-yl](3R,5S)-3,5-dihydroxyhept-6-enoic acid TRIS salt (17.7 g) was dissolved in degassed water (120 ml) at 20° C. A solution of calcium chloride dihydrate (2.6 g) in water (25 ml) was added dropwise at about 20° C. over 20 minutes. The mixture was stirred for 60 minutes and the resultant solid filtered. The solid was washed with water (140 ml) and dried under a flow of nitrogen to give non-crystalline calcium salt of (E)-7-[4-(4-fluorophenyl)-6-isopropyl-2-[methyl(methylsulfonyl)amino]pyrimidin-5-yl](3R,5)-3,5-dihydroxyhept-6-enoic acid.

Preparation of the TRIS Salt (E)-7-[4-(4-fluorophenyl)-6-isopropyl-2-[methyl(methylsulfonyl)amino]pyrimidin-5-yl]-(3R,5S)-3,5-dihydroxyhept-6-enoic acid tris(hydroxymethyl)methylammonium salt (TRIS salt) may be prepared as described in (WO 01/60804).

Comparative Paste Strengths

The paste strength of the filtered product was measured after 5 minutes filtration. The sample prepared from TRIS salt at 40° C. had a paste strength of 82%. The sample prepared from TRIS salt at 20° C. had a paste strength of 36%.

The invention claimed is:

1. A non-crystalline calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid having a paste strength greater than 45% w/w.

2. The non-crystalline calcium salt of claim 1 having a paste strength greater than 55% w/w.

3. The non-crystalline calcium salt of claim 1 having a paste strength greater than 65% w/w.

4. The non-crystalline calcium salt of claim 1 having a paste strength greater than 75% w/w.

5. The non-crystalline calcium salt of claim 1 having a paste strength greater than 85% w/w.

6. The non-crystalline calcium salt of claim 1 having a paste strength greater than 95% w/w.

7. A non-crystalline calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid having a specific surface area of less than 1 $m^2/g$.

8. The non-crystalline calcium salt of claim 7 having a specific surface area of less than 0.8 $m^2/g$.

9. The non-crystalline calcium salt of claim 7 having a specific surface area of less than 0.6 $m^2/g$.

10. The non-crystalline calcium salt of claim 7 having a specific surface area of less than 0.4 $m^2/g$.

11. The non-crystalline calcium salt of claim 7 having a specific surface area of less than 0.3 $m^2/g$.

* * * * *